United States Patent [19]
Yui et al.

[11] Patent Number: 6,037,387
[45] Date of Patent: *Mar. 14, 2000

[54] BLOOD-COMPATIBLE MATERIAL OF A SUPRAMOLECULAR STRUCTURE

[75] Inventors: Nobuhiko Yui; Minoru Terano; Hideharu Mori, all of Tatsunokuchimachi, Japan

[73] Assignee: Japan Advanced Institute of Science and Technology, Hokuriku, Ishikawa-ken, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/069,143

[22] Filed: Apr. 29, 1998

[30] Foreign Application Priority Data

May 8, 1997 [JP] Japan .................................. 9-117670

[51] Int. Cl.$^7$ .......................... A01N 1/00; A61K 31/765; A61K 47/36; C08L 5/16
[52] U.S. Cl. ...................... 523/112; 424/78.38; 424/488; 424/529; 424/425; 514/58; 514/772.3; 524/48
[58] Field of Search .......................... 524/48; 424/78.38, 424/488, 425, 529; 514/58, 772.3; 523/112

[56] References Cited

U.S. PATENT DOCUMENTS

| | | | |
|---|---|---|---|
| 4,927,636 | 5/1990 | Hijiya et al. ............................. | 424/488 |
| 5,384,186 | 1/1995 | Trinh ....................................... | 442/102 |
| 5,855,900 | 1/1999 | Nobuhiko ................................ | 424/425 |

FOREIGN PATENT DOCUMENTS

| | | |
|---|---|---|
| 0 730 869 | 9/1996 | European Pat. Off. . |
| 8-92130 | 4/1996 | Japan . |
| WO 90/03406 | 4/1990 | WIPO . |
| WO 96/09073 | 3/1996 | WIPO . |

OTHER PUBLICATIONS

Wataru Kamimura, et al., Journal of Controlled Release, vol. 44, No. 2/03, pp. 295 to 299, "Interaction of Supramolecular Assembly with Hairless Rat Stratum Corneum", Feb. 17, 1997.

Shoji Nagaoka, et al., Biomaterials, vol. 11, No. 2, pp. 119 to 121, "Clinical Application of Antithrombogenic Hydrogel with Long Poly(ethylen oxide) Chains", Mar. 1990.

*Primary Examiner*—Peter A. Szekely
*Attorney, Agent, or Firm*—Oblon, Spivak, McClelland, Maier & Neustadt, P.C.

[57] ABSTRACT

A platelet metabolism suppressing blood compatible material has a supramolecular structure containing a plurality of cyclic compounds and a hydrophilic straight-chain polymer threading into cavities of the cyclic compounds. Both terminals of the polymer are respectively capped with biodegradable groups having bulks sufficient to prevent the dethreading of the cyclic compounds.

22 Claims, 2 Drawing Sheets

BLOOD-COMPATIBLE MATERIAL OF A SUPRAMOLECULAR STRUCTURE

BACKGROUND OF THE INVENTION

The present invention relates to a blood-compatible supramolecular material, and more particularly, to a blood-compatible material of a supramolecular structure, capable of suppressing the metabolism of platelets.

Medical apparatus which are brought into contact with blood, such as artificial organs, extracorporeal blood circulation circuits and blood bags, are required to have a highly reliable blood compatibility.

Conventionally, such medical apparatus are made of polyolefin-based resins such as polypropylene and polyethylene, since such resins have a high mechanical strength and they can be easily formed. However, the conventional polymeric materials used for manufacturing the medical apparatus are not blood-compatible. Thus the conventional medical apparatus must be used along with an anti-blood coagulant. However, in consideration of possible adverse influences on human body or blood, the time of continuous use of the anti-blood coagulant is limited. Accordingly, the medical care which employs such a conventional medical apparatus is very much limited in terms of time.

Under these circumstances, a great number of researches have been and are presently conducted in order to develop a material exhibiting an excellent blood compatibility. As a typical example thereof, there is a method of fixing an anti-thrombus agent, such as heparin, on a surface of a medical care apparatus, which is brought into contact with blood. However, such a method requires a treatment of fixing the anti-thrombus agent for each and every medical apparatus, and therefore it is not efficient and further entails the drawback of lowering the anti-thrombus property, caused by, for example, peeling off of the anti-thrombus agent.

BRIEF SUMMARY OF THE INVENTION

Thus, an object of the present invention is to provide a blood-compatible material which does not require a modification of its surface, and exhibiting an excellent compatibility by itself.

The above object has been achieved according to the present invention by a platelet metabolism-suppressing blood compatible material of a supramolecular structure comprising a plurality of cyclic compounds and a hydrophilic straight-chain polymer threading into cavities of the cyclic compounds, wherein both terminals of the straight-chain polymer are respectively capped with biodegradable groups having bulks sufficient to prevent the dethreading of the cyclic compounds.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinbefore.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
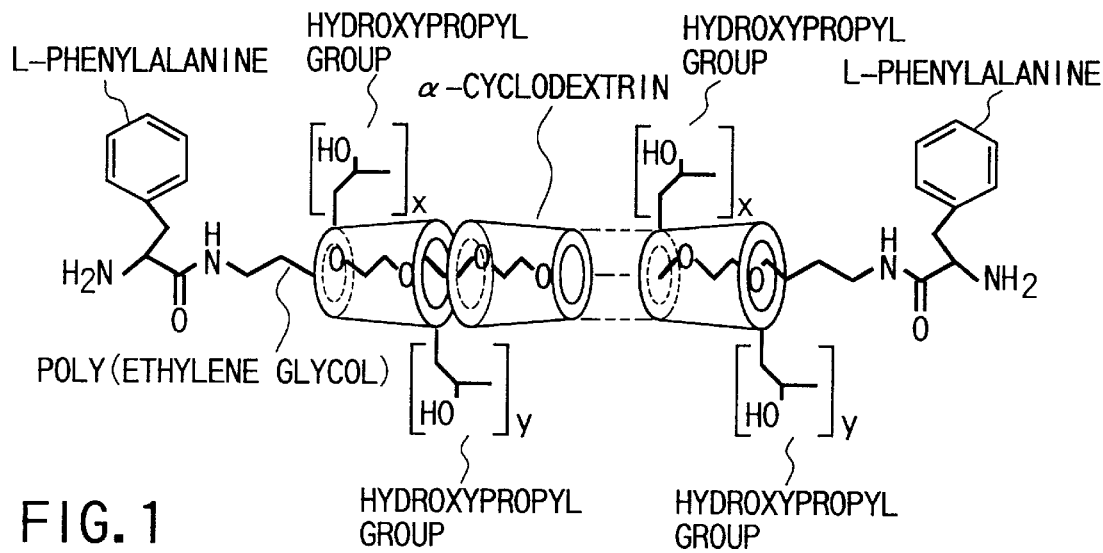
FIG. 1 is a view schematically showing a structure of the blood-compatible material of the present invention.

The present invention has been achieved not from the approach of the conventional designing of the blood-compatible material, but on the basis of the finding that polyrotaxanes of a supramolecular structure in which a straight-chain polymer threads into a plurality of cyclic compounds, serve to suppress the metabolism of blood platelets.

Recently, the researches in the field of supramolecular chemistry on polyrotaxanes having a structure in which a high molecular chain threads into a great number of cyclic compounds, are very popular. For example, Jap. Pat. Appln. KOKAI Publication No. 8-92130 discloses a biodegradable medicine-polymer aggregate of a supramolecular structure including a plurality of medicine-bonded cyclic compounds prepared by bonding medicine to cyclodextrins, and a straight-chain polymeric compound threading into the cavities of these cyclic compounds.

The inventors of the present invention have found that a certain type of polyrotaxane suppresses or inhibits the metabolism of platelets, and therefore such a polyrotaxane exhibits an excellent blood compatibility by itself, and based on this finding, they have accomplished the present invention.

The cyclic compounds used in the present invention are preferably selected from the group consisting of α-cyclodextrin, β-cyclodextrin, γ-cyclodextrin and a mixture of these. Of these, α-cyclodextrin is particularly preferable.

In the present invention, the straight-chain hydrophilic polymer threading into the cavities of the cyclic compounds has a biocompatibility, and preferable examples thereof are polyethylene glycol (sometimes referred to as PEG) and copolymers of polyethylene glycol and polypropylene glycol. It is preferable that these straight-chain hydrophilic polymers should have the number average molecular weight of 200 to 10,000, and more preferably, 400 to 5,000. It is preferable that the copolymers of polyethylene glycol and polypropylene glycol should contain polyethylene glycol in an amount of 10 to 90 mole %, more preferably, 30 to 60 mole %. If these straight-chain hydrophilic polymers are of the type having bulky groups at both terminals from the beginning, the cavities of the cyclic compounds are not threaded into by such a polymer. Therefore, those polymers having such small groups as methyl group, methoxy group and amino group, that do not block the threading of the hydrophilic polymer into the cyclic compounds, at both terminals, should be employed to be first threaded into the cavities of the cyclic compounds.

The hydrophilic polymer can thread into the cavities of the cyclic compounds by a simple operation of adding an aqueous solution of the hydrophilic polymer compound dropwise to a saturated aqueous solution of the cyclic compound, followed by stirring. With this operation, a supramolecular structure (polyrotaxane), in which a hydrophilic polymer compound threads into the cavities of cyclic compounds, can be obtained in the form of precipitate.

After obtaining the polyrotaxane in which a straight-chain hydrophilic polymer threads into the cavities of a plurality of cyclic compounds, both terminals of the straight-chain polymer are respectively capped with biodegradable groups having bulks sufficient to prevent the dethreading of the cyclic compounds.

It is preferable that the biodegradable groups should be made of an oligopeptide chain whose unit is an amino acid such as alanine, valine, leucine, isoleucine, methionine, proline, phenylalanine, triptophan, aspartic acid, glutamic acid, glycine, serine, threonine, thyrosin, cystein, lysine, arginine or histidine, or an oligosaccharide chain whose constituent unit is a sugar such as dextrin, hyaluronic acid, chitin, chitosan, arginic acid, chondroitin sulfate, starch or pullulan. The oligopeptide chain and oligosaccharide chain each should preferably contain 1 to 5 constituent units, and the units may be of the same type, or different types.

These biodegradable group can be introduced by a method known per se in the art, for example, the transesterification.

With regard to the blood-compatible material of a supramolecular structure, consisting of a straight-chain hydrophilic polymer threading into the cavities of cyclodextrins, it has been found that the material will exhibit even more effective blood-compatibility when the cyclodextrins are hydroxypropylated. A model structure of such a blood-compatible material of a supramolecular structure (that is, HP-α/E-PHE synthesized in the following example) is schematically shown in FIG. 1. As can be seen in FIG. 1, the supramolecular structure consists of a plurality of α-cyclodextrins and a polyethylene glycol threading into the cavities of the α-cyclodextrins, in which L-phenylalanin is introduced and bonded to both terminals of polyethylene glycol. Each α-cyclodextrin contains hydroxypropyl groups as a result of the hydroxypropylation. It is preferred that 2 to 16, more preferably 6 to 9 hydroxypropyl groups should be present per one cyclodextrin molecule such as α-cyclodextrin.

The blood-compatible material of the present invention has a polyrotaxane structure (supramolecular structure) in which a straight-chain hydrophilic polymer threading into the cavities of a plurality of cyclic compounds (α-cyclodextrin and the like), and therefore the material serves to enhance the membrane fluidity of blood cells brought into contact with the material. Further, in connection with this, the material can suppress an increase in cytoplasmic free calcium concentration, and regulate the intracellular metabolism in blood cells, which depends upon the calcium concentration. The biodegradable groups at both terminals of the hydrophilic polymer are decomposed by an enzyme, thus releasing all of the cyclic compounds threaded into by the polymer at once, and they are absorbed in vivo and excreted.

EXAMPLES

<Synthesis of Blood-compatible Material>

To saturated aqueous solutions of α-cyclodextrin (α-CD), 10 wt % aqueous solutions of α[-(2-Amino-2-ethylmethyl)-x-oxypropyl]-ω-(amino-y-oxypropyl) polyethyleneglycol (x+y=2.5) with a number average molecular weight Mn of polyethylene glycol of 2000 (hereinafter "PEG-BA 2000", supplied by Suntechno Chemical Co., Tokyo, Japan, as JEFFAMINE® ED-2001) and α-(3-Aminopropyl)-ω-(3-aminopropyl) polyethylene glycol with Mn of 4000 (hereinafter "PEG-BA 4000", supplied by Sanyo Chemical Co. Ltd., Kyoto, Japan, as IONET® YB-400) were added respectively in droplets, and stirred to give white precipitates (polyrotaxanes), respectively.

The amino groups at both terminals of each PEG were capped with L-phenylalanine (L-Phe) by transesterification as follows.

Benzyloxycarbonyl (to be abbreviated as Z)-L-Phe (supplied by Wako Pure Chemical Co. Ltd) was dissolved in dry dimethylsulfoxide (DMSO), followed by the addition of the respective polyrotaxane. Then, DMSO was added to the resultant suspension until homogeneous and stirred at room temperature for 48 hours.

The obtained polyrotaxanes whose both terminals were capped with Z-L-Phe (α/E2-PHE-Z and α/E4-PHE-Z, respectively; where E2 represents the polyrotaxane having PEG of Mn of 2000, and E4 represents the polyrotaxane PEG of Mn of 4000) were reacted with propylene oxide in 1N aqueous NaOH solution at room temperature for 24 hours. After neutralization with aqueous HCl solution, the resultant solution was dialyzed against water and the resultant product was lyophilized. Thus, Z-L-Phe-terminated hydroxypropylated polyrotaxanes were obtained.

Finally, the Z-group in each of Z-L-Phe-terminated polyrotaxanes was removed under a hydrogen atmosphere with palladium-carbon to give hydroxypropylated polyrotaxanes (HP-α/E2-PHE and HP-α/E4-PHE). (When they are called collectively, the general term, HP-α/E-PHE will be used hereinafter.)

The number of α-CDs in HP-α/E2-PHE and HP-α/E4-PHE was determined to be about 11 and 22, respectively, by $^1$H-NMR. The degree of hydroxypropylation (that is, the number of hydroxypropyl group per each α-CD) was also determined to be 8 per α-CD in both HP-α/E2-PHE and HP-α/E4-PHE by $^1$H-NMR.

As reference samples, hydroxypropylated-α-CD (HP-α-CD) and L-Phe-terminated PEGs (E2-PHE and E4-PHE, and they will sometimes be collectively referred to as "E-PHE" hereinafter) were prepared as follows:

(1) HP-α-CD was obtained by hydroxypropylating α-CD by the same manner as in the case of HP-α/E-PHEs. The degree of hydroxypropylation was determined to be 8 per α-CD by $^1$H-NMR.

(2) E2-PHE and E4-PHE were synthesized by reacting Z-L-Phe-succinimide, and PEG-BA 2000 and PEG-BA 4000, respectively, in DMF. The reaction mixtures were poured into excess dry ether, and then washed with ether to give E2-PHE and E4-PHE.

<Measurements of Properties of Polyrotaxanes by Static Light Scattering (SLS) measurements>

The weight average molecular weight (Mw), association number, second virial coefficient ($A_2$) and the radius of gyration (Rg) of HP-α/E-PHEs were determined by SLS measurements using a light scattering instrument (Otsuka Electronics, Co., Osaka, Japan, DLS-7000), equipped with a 10 mW He-Ne laser (having wavelength of 633 nm).

More specifically, 0.2 g of HP-α/E-PHE was dissolved in 10 ml of 0.05M phosphate buffer solution (PBS) having pH of 7.4, and stirred for 48 hours at 37° C. The resultant solution was filtered through a filter with a pore size of 0.45 µm, and diluted samples were prepare at the range of 0.5–8.0 mg/ml. These sample solutions were transferred into a light scattering cell through a filter with a pore size of 0.2 μm. Measurements were carried out over the angular range from 30 to 150° at 37±0.5° C.

As in the same manner, SLS measurements of HP-α-CD, and E-PHE were examined.

The refractive index increment of HP-α/E2-PHE and HP-α/E4-PHE solutions at 37° C. were determined to be 0.16 and 0.14 mg/litter (L), respectively, by using a double beam differential refractometer (Otsuka Electronics, Co., Osaka, Japan, DRM-1030). The Mw, $A_2$, and Rg values of HP-α/E-PHEs and E-PHEs were obtained from plots of (Kc/R(θ)) vs. $\sin^2$ (θ/2) (Zimm plot), where K is a combination of known optical constant, c is the concentration, and R(θ) is the Rayleigh ratio. The Mw and $A_2$ values of HP-α-CD were obtained by (Kc/R(θ)) vs. c (Debye plot) at a concentration range of 10–50 mg/ml. It should be noted that E2-PHE was not completely dissolved at a concentration range of 10–50 mg/ml and therefore only the portion soluble in the PBS was measured. Further, the Mw and $A_2$ values of HP-α-CD were obtained by Debye plot, and therefore the Rg value of HP-α-CD was not determined.

The association number was estimated from the weight average molecular weight obtained and the molecular weight of monomer. The results of the SLS measurements are summarized in TABLE 1 below. As can be seen in TABLE 1, the estimated association numbers of HP-α/E2-PHE and HP-α were both about 2, and the estimated association number of HP-α/E4-PHE was about 20. Further, the estimated association number of E-PHE was about 50. The $A_2$ values of HP-α/E-PHE and HP-α-CD were $2 \times 10^4$ to $6 \times 10^4$ mL·mole/g$^2$, whereas that of E-PHE was $0.25 \times 10^4$ to $0.90 \times 10^4$ mL·mole/g$^2$. The values of HP-a/E-PHE and its constituent molecules are in a range of 64 to 150 nm.

calcium concentration was 1 mM just prior to use in HP-α/E-PHE measurements.

100 μl of 10 wt. % HP-α/E-PHE solution in HBSS was mixed with 400 μl of the above Fura 2-AM-loaded platelet suspension, and stirred in a fluorescence cuvette in a fluorimeter (Japan Spectroscopic Co., Tokyo, Japan, model CAF-100) equipped with a magnetic stirrer, at 37° C. Then, thrombin was added to the mixture. The mixture was excited at both 340 and 380 nm and emission was measured at 500 nm. Fluorescence intensities at each of the two wavelengths were used to determine the fluorescence dichroic ratio 340/380 (R). The cytoplasmic free calcium concentration, $[Ca^{2+}]_i$ was calculated based on the R value by the same manner as reported in J. Biol. Chem., 260, 3440 (1985) by G. Grynkiewicz et al.

As a control, 100–200 nM $[Ca^{2+}]_i$ in unused platelets is checked prior to the mixing with the solution. In order to minimize time-dependent effects on platelet functions or leakage of Fura 2-AM, these experiments were completed within 1 h of Fura 2-AM loading.

As the same manner, $[Ca^{2+}]_i$ was calculated for constituent molecules of polyrotaxanes and their mixture.

Figure 2:
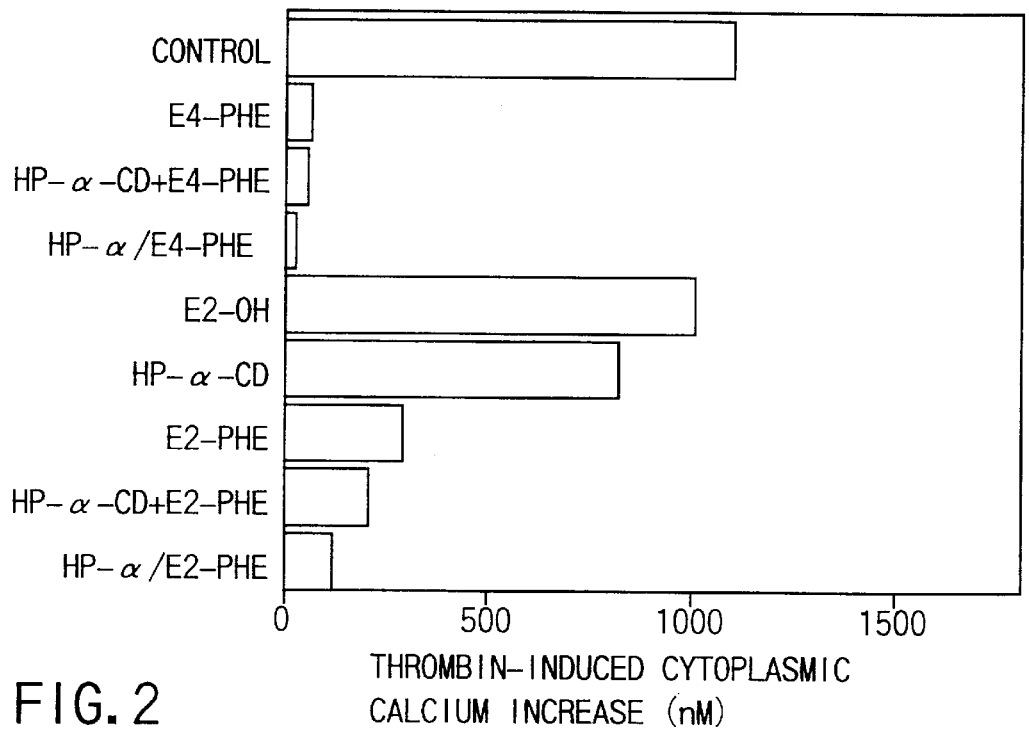
FIG. 2 is a graph illustrating the suppressing effect of the blood compatible material of the present invention, with respect to an increase in cytoplasmic free calcium, induced by thrombin, along with comparative examples.

As a result, few change in the fluorescence ratio of Fura 2-AM was observed when HP-a/E-PHE solution was added to the platelet suspension. This observation indicates that HP-α/E-PHEs did not induce cytoplasmic free calcium concentration $[Ca^{2+}]_i$ increase, i.e., platelets were not activated by HP-α/E-PHEs. Then, thrombin (final concentration: 0.1 unit/ml) was added to the platelet suspension 1 min after mixing with HP-α/E-PHE solution. Thrombin-induced cytoplasmic free calcium concentration $[Ca^{2+}]_i$ increase was significantly inhibited by the addition of HP-α/E2-PHE solution (FIG. 2).

TABLE 1

Properties of HP-α/E4-PHE, etc. determined by measurement of static light scattering

|  | Weight average molecular weight ($\times 10^4$) (g/mol) | Number average molecular weight (calculated value: $\times 10^4$) | Number of association | $A_2$ ($\times 10^{-4}$) (ml · mol/g$^2$) | $R_G$ (nm) |
|---|---|---|---|---|---|
| HP-α/E4-PHE | 6.64 | 3.77 | 2 | 3.51 | 91.3 |
| HP-α/E2-PHE | 40.4 | 2.04 | 20 | 2.34 | 150.7 |
| HP-α-CD | 0.32 | 0.144 | 2 | 5.94 |  |
| E4-PHE | 20.2 | 0.441 | 46 | 0.245 | 63.6 |
| E2-PHE | 12.7 | 0.229 | 55 | 0.895 | 101.6 |

<Measurement of cytoplasmic free calcium change in platelets>

Cytoplasmic free calcium concentration ($[Ca^{2+}]_i$ in platelets was examined using platelet suspension loaded with 1-(2-(5'-carboxyoxazol-2'-il)-6-amonobenzofuran-5-oxy)-2-(2'-amino-5'-methylphenoxy)ethane N,N,N',N'-pentaacetoxymethylester tetraacetate (Fura 2-AM), by the same manner as that of J. Biomater. Sci. Polym. Edn. 4, 199 (1993) and J. Biomater. Sci. Polym. Edn. 4, 199 (1993) by Yui et al.

Platelet suspension in $Ca^{2+}$- and $Mg^{2+}$-free Hanks' balanced salt solution (HBSS) (platelet concentration: $3 \times 10^8$/ml) was prepared from citrated blood of male Japanese white rabbits, weighing 2.5–3.0 kg. Fura 2-AM was loaded into platelets by incubating the platelet suspension with Fura 2-AM solution at 37° C. for 60 minutes at a Fura 2-AM concentration of 5 μM. The platelets were washed with HBSS and were finally resuspended in HBSS, so that the final platelet concentration was $3 \times 10^8$/ml. The platelet suspension was recalcified with $CaCl_2$, so that the external As to reference samples, a mixture of HP-α-CD and E2-PHE (HP-α-CD+E2-PHE) and E2-PHE showed lower inhibitory effect on $[Ca^{2+}]_i$ increase although other constituent molecules, HP-α-CD and PEG (E2-OH), showed no inhibitory effect (FIG. 2).

<Evaluation of Blood Cell Membrane Fluidity>

It has been reported that any physicochemical changes in plasma membranes including enhanced fluidity dominate the function of membrane proteins and/or intracellular metabolism of a certain cell systems (Biochem. Biophys. Acta, 886, 109 (1986) by C. H. Bamford et al. and Proc. Natl. Acad. Sci., 76, 368 (1979)). From this perspective, the effect of the polyrotaxanes on plasma membrane fluidity was examined using DPH-loaded RBC ghost suspension.

More specifically, citrated blood of male Japanese white rabbits weighing 2.5–2.8 kg was collected and centrifuged at 1000 rpm for 15 min to obtain red blood cells (RBCs). RBCs were washed with 0.155M NaCl solution (pH 7.4), and centrifuged at 1000 rpm for 10 min two times. The suspension was washed with 15–20 fold volumes of 0.01M PBS (pH 7.4) several times. After centrifugation at 18000 rpm for 30 min at 4° C., the obtained RBC ghost suspension was adjusted at 0.1 mg prot.·mL$^{-1}$ with 0.155M NaCl solution (pH 7.4) by a micro BCA method, discussed in Anal. Biochem. 150,76 (1985) by P. K. Smith et al. 1,6-diphenyl-1,3,5-hexatriene (DPH) (Wako Pure Chemical Co. Ltd.) solution in tetrahydrofuran (2 mM) was diluted into RBC ghost suspension to 2 μM and incubated with gentle agitation at 37° C. for 60 min in the dark.

Fluorescence anisotropy of DPH in RBC ghosts was measured in order to assess the membrane fluidity. Fluorescence emission spectra (360–500 nm) of DPH-loaded RBC ghosts were checked at excitation wavelength of 360 nm. 100 μl of polyrotaxane solution in 0.155M NaCl solution (pH 7.4) was mixed with 400 μl of DPH-loaded RBC ghost suspension in a fluorescence cuvette in a spectrofluorimeter (Japan Spectroscopic Co., Tokyo, Japan, FP-777) equipped with a fluorescence polarization accessory (Japan Spectroscopic Co., Tokyo, Japan, ADP-300) at 37° C. with magnetic stirring. DPH was excited at 360 nm and the fluorescence was detected at 430 nm. The slit widths for both excitation and emission were 10 nm. Fluorescence intensities were measured with polarizers inserted into the excitation and emission light paths. Fluorescence anisotropy, $<r>$, was calculated by the following equation:

$$<r> = (I_H - I_{Hb}) - G(I_V - I_{Vb})/((I_H - I_{Hb}) + 2G(I_V - I_{Vb}))$$

where $I_H$ and $I_V$ are emission intensities observed with the analyzing polarizer horizontal and vertical to the polarized excitation beam; $I_{Hb}$ and $I_{Vb}$ are fluorescence intensities for blank solution (0.155M NaCl solution) at the same position of the polarizer as $I_H$ and $I_V$; and G is a correction factor, equal to $I_{V'}/I_{H'}$, the primes indicating excitation polarized in a horizontal direction.

As the same manner, $<r>$ was measured for constituent molecules of HP-α/E-PHEs and their mixture.

Figure 3:
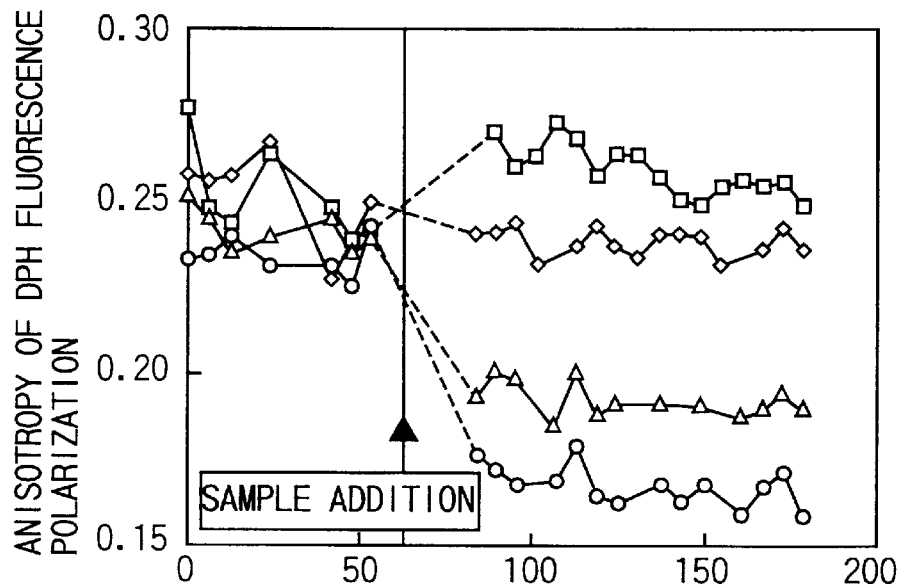
FIG. 3 is a graph illustrating the anisotropy of DPH fluorescence polarization.
Figure 4:
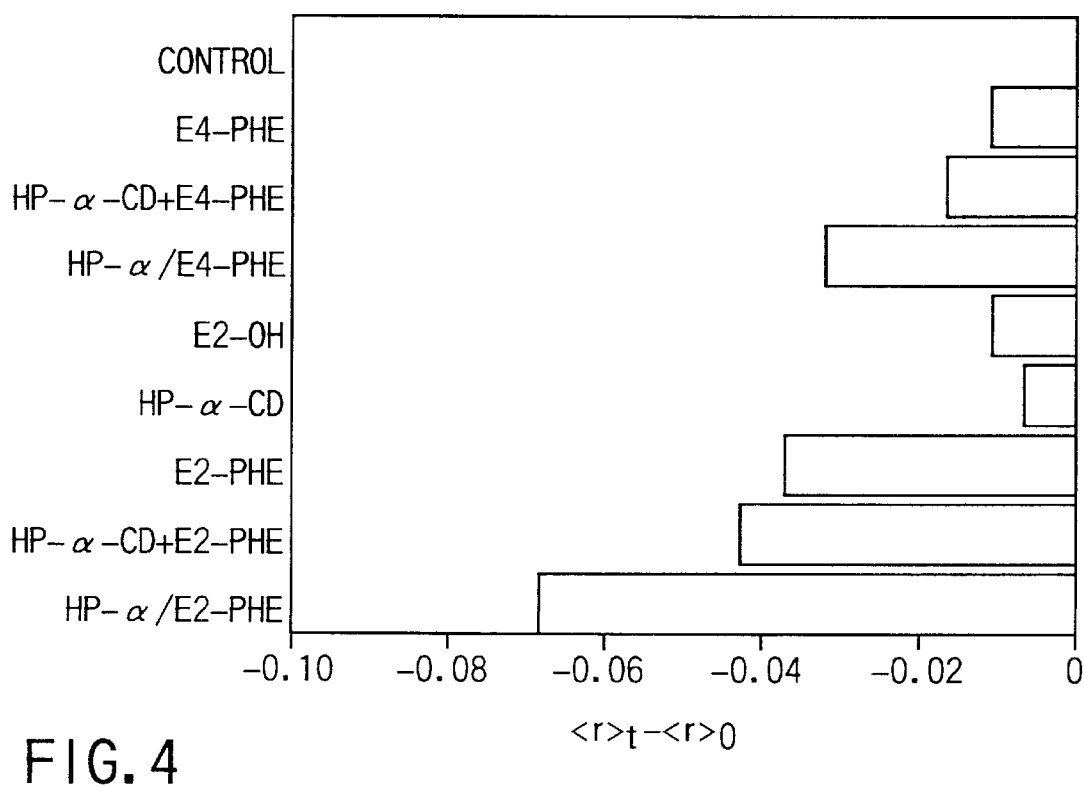
FIG. 4 is a graph illustrating the effect of the blood-compatible material of the present invention, with respect to the membrane fluidity.

Fluorescence anisotropy, $<r>_0$, was approximately 0.23–0.27 in unused RBC ghosts, being consistent with the reported $<r>_0$ value (Neurochem., 38, 1699 (1982) by C. Sambilla). As shown in FIG. 3, $<r>$ was immediately decreased by the addition of HP-α/E-PHE solution, indicating an increase in the membrane fluidity of RBC ghosts. (In FIG. 3, the line plotted with ◇ indicates the case of the control (0.155M NaCl), the line plotted with □ indicates the case of HP-α-CD, the line plotted with Δ indicates the case of the mixture of HP-α-CD and E2-PHE, and the line plotted with ○ indicates the case of HP-α/E2-PHE.) FIG. 4 summarizes the changes in $<r>$ by the addition of HP-α/E-PHE solutions ($<r>_t - <r>_0$), along with the changes by the addition of its constituent molecules and mixtures. As can be seen from FIG. 4, HP-α/E2-PHE induced a significant decrease in $<r>$, although HP-α-CD+E2-PHE and E2-PHE showed a fewer effects on membrane fluidity. HP-α-CD and E2-OH showed no effects on membrane fluidity. Such specific phenomenon of the polyrotaxane was also observed in the case of PEG $M_n$ of 4000 (HP-α/E4-PHE).

As can be understood from the above results, the blood compatible material of the present invention, made of polyrotaxane is capable of effectively inhibiting or suppressing an increase in thrombin-induced cytoplasmic free calcium concentration. As particularly seen in the case of HP-α/E2-PHE, these effects of the polyrotaxanes were more significant than their constituent molecules (such as a mixture of HP-α-CD and L-Phe-terminated PEGs). Further, enhanced membrane fluidity of RBC ghosts was most significantly observed with the blood compatible material of the present invention. Furthermore, SLS study revealed that specific supramolecular association of the polyrotaxanes existed due to hydrophilic-hydrophobic balance of threaded HP-α-CDs and terminal L-Phe moieties. These findings is of great importance for regulating intracellular metabolism in blood cells by these polyrotaxanes. Each of the molecules constituting the blood compatible material of the present invention is harmless to organism. The biodegradable groups at the terminals of hydrophilic polymer is decomposed by an enzyme, and therefore all of the cyclic compounds threaded into by the straight-chain hydrophilic high molecule are released at one time, to be absorbed in vivo, and excreted.

As described above, according to the present invention, there is provided a blood compatible material capable of suppressing the metabolism of platelets, and exhibiting an excellent blood compatibility by itself. The blood compatible material is metabolized as it is decomposed and absorbed in body, and therefore it can be applied not only to exteracorporeal medical apparatus which is brought into contact with blood, such as artificial organs, blood bags and extracorporeal blood circulation circuits, but also to intracorporeal enthetic micromachines for medical care.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. A method of suppressing blood platelet metabolism, comprising contacting blood with a blood platelet metabolism suppressor having a supramolecular structure which comprises:
   a plurality of cyclic compounds having cavities, and
   a hydrophilic straight-chain polymer threading into the cavities of said cyclic compounds, wherein the terminals of said polymer are capped with biodegradable groups having sufficient bulk to prevent the dethreading of said cyclic compounds from the chain of said polymer.

2. The method of claim 1, wherein said cyclic compounds comprise one or more cyclodextrins.

3. The method of claim 2, wherein said one or more cyclodextrins are selected from the group consisting of α-cyclodextrin, β-cyclodextrin, γ-cyclodextrin, hydroxypropylated α-cyclodextrin, hydroxypropylated β-cyclodextrin, and hydroxypropoylated γ-cyclodextrin.

4. The method of claim 3, wherein said said one or more cyclodextrins is hydroxypropylated α-cyclodextrin.

5. The method of claim 4, wherein said hydroxypropylated α-cyclodextrin contains 2 to 16 hydroxypropyl groups per cyclodextrin molecule.

6. The method of claim 1, wherein said straight-chain polymer is a polyethylene glycol having a number average weight of 200 to 10,000.

7. The method of claim 6, wherein the polymer is a copolymer of polyethylene glycol and polypropylene glycol, which has a number average weight of 200 to 10,000 and contains polyethylene glycol in an amount of 10 to 90 mol %.

8. The method of claim 1, wherein the polymer has a number average molecular weight of from 200 to 10,000.

9. The method of claim 1, wherein the polymer has a number average molecular of 400 to 5,000.

10. The method of claim 1, wherein the biodegradable groups are oligosaccharide chains containing from 1 to 5 repeating units of at least one member selected from the group consisting of dextran, hyaluronic, chitin, chitosan, alginic acid, chondroitin sulfate, starch and pullulan.

11. The method of claim 1, wherein the biodegradable groups are peptide chain containing from 1 to 5 repeating units of at least one member selected from the group consisting of alanine, valine, leucine, isoleucine, methionine, proline, phenylalanine, tryptophan, aspartic acid, glutamic acid, glycine, serine, threonine, tyrosine, cystine, lysine, arginine, and histidine.

12. A method of suppressing blood platelet metabolism, comprising contacting blood with a blood platelet metabolism suppressor having a supramolecular structure which consists of:

one or more cyclodextrins selected from the group consisting of α-cyclodextrin, β-cyclodextrin, γ-cyclodextrin, hydroxypropylated α-cyclodextrin, hydroxypropylated β-cyclodextrin, and hydroxypropoylated γ-cyclodextrin, and a hydrophilic straight-chain polymer threading into the cavities of said one or more cyclodextrins, wherein the terminals of said polymer are capped with biodegradable groups having sufficient bulk to prevent the dethreading of said one or more cyclodextrins from the chain of said polymer.

13. The method of claim 12, wherein said said one or more cyclodextrins is hydroxypropylated α-cyclodextrin.

14. The method of claim 13, wherein said hydroxypropylated α-cyclodextrin contains 2 to 16 hydroxypropyl groups per cyclodextrin molecule.

15. The method of claim 12, wherein said straight-chain polymer is a polyethylene glycol having a number average weight of 200 to 10,000.

16. The method of claim 12, wherein said straight-chain polymer is a copolymer of polyethylene glycol and polypropylene glycol, which has a number average weight of 200 to 10,000 and contains polyethylene glycol in an amount of 10 to 90 mol %.

17. The method of claim 12, wherein the polymer has a number average molecular weight of from 200 to 10,000.

18. The method of claim 12, wherein the polymer has a number average molecular of 400 to 5,000.

19. The method of claim 12, wherein the biodegradable groups are oligosaccharide chains containing from 1 to 5 repeating units of at least one member selected from the group consisting of dextran, hyaluronic, chitin, chitosan, alginic acid, chondroitin sulfate, starch and pullulan.

20. The method of claim 12, wherein the biodegradable groups are peptide chain containing from 1 to 5 repeating units of at least one member selected from the group consisting of alanine, valine, leucine, isoleucine, methionine, proline, phenylalanine, tryptophan, aspartic acid, glutamic acid, glycine, serine, threonine, tyrosine, cystine, lysine, arginine, and histidine.

21. The method of claim 1, wherein the biodegradable groups at the terminals of the hydrophilic polymer are degraded by enzymes in the blood, thereby releasing the cyclic compound threaded into the polymer.

22. The method of claim 12, wherein the biodegradable groups at the terminals of the hydrophilic polymer are degraded by enzymes in the blood, thereby releasing the cyclic compound threaded into the polymer.

* * * * *